(12) United States Patent
Dorn

(10) Patent No.: US 6,716,632 B1
(45) Date of Patent: Apr. 6, 2004

(54) SYSTEM FOR STABILIZING SAMPLES

(76) Inventor: Gordon L. Dorn, 29323 Gimpl Hill Rd., Eugene, OR (US) 97402-9054

( * ) Notice: Subject to any disclaimer, the term of this patent is extended or adjusted under 35 U.S.C. 154(b) by 0 days.

(21) Appl. No.: 10/048,660

(22) PCT Filed: Apr. 18, 2000

(86) PCT No.: PCT/US00/10384
§ 371 (c)(1),
(2), (4) Date: May 7, 2002

(87) PCT Pub. No.: WO01/08489
PCT Pub. Date: Feb. 8, 2001

Related U.S. Application Data
(60) Provisional application No. 60/146,729, filed on Aug. 2, 1999.

(51) Int. Cl.[7] .............................................. G01N 33/493
(52) U.S. Cl. ............................. 436/18; 422/28; 422/40; 435/243; 435/260; 436/8; 252/380
(58) Field of Search .................... 422/28, 40; 435/260, 435/243, 1.1, 2, 307.1, 264; 436/18, 8; 252/380, 397

(56) References Cited

U.S. PATENT DOCUMENTS

| | | | | |
|---|---|---|---|---|
| 4,200,651 A | * | 4/1980 | Borjesson et al. | 514/626 |
| 4,258,032 A | * | 3/1981 | Mehl | 424/659 |
| 4,390,442 A | | 6/1983 | Quick | 252/106 |
| 4,836,986 A | | 6/1989 | Ogunbiyi et al. | 422/28 |
| 4,880,602 A | * | 11/1989 | Al-Sioufi | 422/28 |
| 5,532,224 A | * | 7/1996 | Desai et al. | 510/112 |
| 5,670,160 A | | 9/1997 | Eggensperger et al. | 424/405 |
| 5,696,171 A | * | 12/1997 | Rupp et al. | 514/700 |
| 6,231,849 B1 | * | 5/2001 | Schiller | 424/84 |
| 6,261,844 B1 | * | 7/2001 | Smith et al. | 436/18 |
| 6,482,799 B1 | * | 11/2002 | Tuse et al. | 514/14 |

FOREIGN PATENT DOCUMENTS

| | | |
|---|---|---|
| EP | 0 180 309 A1 | 5/1986 |
| EP | 0 231 080 A1 | 8/1987 |
| EP | 0 605 321 A1 | 7/1994 |
| EP | 0 628 314 A1 | 12/1994 |
| WO | WO96/29867 A2 | 10/1996 |
| WO | WO98/52612 A1 | 11/1998 |

OTHER PUBLICATIONS

I. A. Porter and J. Brodie, "Boric Acid Preservation of Urine Samples", *British Medical Journal*, vol. 2, May 10, 1969, (3 pages).

K. L. Guenther and J. A. Washington, II, "Evaluation of the B–D Urine Culture Kit", *Journal of Clinical Microbiology*, vol. 14, No. 6, Dec. 1981 (pp. 628–630).

Gordon L. Dorn, Barbara Ann Brown, Richard L. Cohen, John A. Moore, J. F. Barlow, Paul M. Southern, Jr., June Ketchum, and John Sloan Leonard, "Adherence to Laboratory Guidelines: A Study on Urine Specimen Transit Time", *Diagnostics & Clinical Testing*, vol. 27, Jun. 1989, (pp. 28–31).

Gordon L. Dorn, "Microbial Stabilization of Antibiotic–Containing Urine Samples by Using the FLORA–STAT Urine Transport System", *Journal of Clinical Microbiology*, vol. 29, No. 10, Oct. 1991, (pp. 2169–2174).

Peter J. Howanitz, Andrew J. Saladino, and Jane C. Dale, "Timeliness if Urinalysis, A College of American Pathologists Q–Probes Study of 346 Small Hospitals", *Arch Pathol Lab Med*, vol. 121, Jul. 1997 (pp. 667–672).

"Recommendations Regarding the Use of Vaccines That Contain Thimerosal as a Preservative", *MMWR*, vol. 48, No. 43, Nov. 5, 1999 (pp. 996–999).

* cited by examiner

Primary Examiner—Robert J. Warden, Sr.
Assistant Examiner—Sean E. Conley
(74) Attorney, Agent, or Firm—Sidley Austin Brown & Wood LLP

(57) ABSTRACT

A transport/preservation system has been found which provides safe, effective transport for patient specimens and bodily fluids, and functions as a preservative for biological reagents, therapeutics and personal care products. The transport/preservative formulations can also be used as safe, effective sanitizers on surfaces, equipment, and appliances. The transport preservation formulations comprising a biguanide and one or more other antimicrobial agents are cidal to microorganisms when present in a sample or on a surface to be sanitized.

28 Claims, No Drawings

SYSTEM FOR STABILIZING SAMPLES

CROSS-REFERENCE TO RELATED APPLICATION

This application claims the benefit of U.S. Provisional Application No. 60/146,729, filed Aug. 2, 1999.

TECHNICAL FIELD

This application relates to stabilization and preservation of patient specimens, bodily fluids, therapeutics, personal care products, surface sanitizers or biological reagents.

BACKGROUND OF THE INVENTION

Diagnostic laboratory tests on patient bodily fluids or tissue specimens provide significant information for disease treatment. These tests aid in discovery of occult disease, early diagnosis after the onset of signs and symptoms, differential diagnosis of various possible diseases, determination of the stage of the disease, estimation of the activity of the disease, detection of recurrence of disease, and measurement of the efficacy of therapy. The diagnostic benefits of many laboratory tests, however, require that the chemical and physical properties of a patient's sample remain substantially unaltered during transport, i.e., the time required to go from sample collection from the patient to processing and/or testing by the laboratory.

Microbial contamination of a patient's sample can cause significant changes to its physical and biochemical composition during transport. If the bioburden of a sample is low and the sample is processed within a short time (2 to 4 hours) after collection, the microorganisms present usually will not affect the sample's chemical properties. However, if the sample can sustain the growth of organisms and the time between collection and processing exceeds 4 hours, the growth and/or metabolism of the microorganisms can alter the chemical and/or physical properties of the sample. For example, the organisms may be able to consume certain components present in the sample such as carbon, nitrogen, or minerals, thus, removing or altering components which were present in the sample at the time of collection. Secondly, as a result of microbial growth, metabolism or death, components which were not present at the time of collection may be released into the sample.

One type of patient sample which is greatly affected by microbial contamination during transport is a urine sample submitted for urinalysis. Urinalysis is a series of tests performed on the urine sample including leukocytes, cast cells, red blood cells, glucose, bilirubin, ketone, specific gravity, pH, protein, urobilinogen, nitrite, and blood. Normal healthy women have $10^2$–$10^3$ microorganisms present in their urine. Microorganisms can also be introduced into the patient's urine sample either through a patient's clinical infection or by inadvertent contamination during the collection process or transport to the laboratory. Since urine samples generally contain sufficient metabolites and other factors required to support the growth and replication of most microorganisms commonly found in urine samples, delays in transport beyond 4 hours can lead to significant changes in the chemical and physical properties of the samples. For example, in one study, common urinary tract contaminants or potential urinary pathogens significantly altered the chemical/physical properties of unpreserved urine held for 8–24 hours or longer at room temperature: false positive reactions for hemoglobin, protein, nitrites, and esterase; false negative reactions for nitrites, glucose, protein and ketones; and substantial changes in pH. Many of these alterations in the chemical properties of the unpreserved urine samples occurred within 8 hours (Dorn, G. L., unpublished).

Laboratory standards recommend that urine samples be analyzed within two hours after collection from the patient to circumvent changes in chemical and physical properties. However, with the emergence of Health Maintenance Organizations (HMO's), Preferred Physician Organizations (PPO's), and centralized laboratory testing facilities combined with increasing pressure to be more cost effective through batch processing of samples, it has become increasingly difficult to comply with traditional standards of practice. For example, one study showed that a large percentage of samples submitted for culture within a hospital setting were >4 hours old prior to processing. (Dorn, et al., "Adherence to laboratory guidelines: a study on urine specimen transport time," *Diagnostics & Clinical Testing* 27:28–31 (1989)). Another study indicated that all samples submitted to centralized commercial laboratories exceeded the recommended time limits for transport. (Dorn, G. L., "Microbial stabilization of antibiotic-containing urine samples by using the FLORASTAT urine transport system," *J Clin Micro* 29:2169–2174 (1991)). In the area of urinalysis, a recent College of American Pathologist Q-Probes Study documented that for inpatients and outpatients, respectively, only 64% and 77% of laboratories were able to meet the 2-hour transport goal 90% of the time. (Howanitz, et al., "Timeliness of urinalysis: a College of American Pathologists Q-probes study of 346 small hospitals," *Arch Pathol Lab Med* 121:667–672 (1997)).

Since current medical practices often prevent expedient transport of urine samples for urinalysis, and since microorganisms are frequently present in urine samples collected for urinalysis, a method of blocking the deleterious effects of microbial contamination on a urine sample during transport is advantageous in preserving the chemical and physical integrity of the sample. For this purpose, various preservatives for urine samples have been developed and commercialized. Among the active ingredients for these preservatives are: boric acid, mercuric oxide, sodium azide, tartaric acid, and thimerosal (ethylmercurithiosalicylic acid). Boric acid has been reported to be compatible as a preservative used in combination with urinalysis and leukocyte/cast cell analysis. (Porter, I. A. and Brodie, J. 1969. "Boric acid preservation of urine samples," *Br Med J* 2:353–355; Guenther, K. L. and Washington II, J. A. 1981. Evaluation of the B-D urine culture kit," *J Clin Microbiol* 14:628–630).

Despite the commercial availability of preservatives for urine samples, there are significant deficiencies associated with them. For example, many of the active ingredients used in commercially available urine preservative systems present health, flammability, and/or reactivity hazards. According to the National Fire Prevention Association's health, flammability, and reactivity hazard ratings for chemicals, a short exposure to mercuric oxide and thimerosal could cause death or major residual injury. Although mercury-based systems such as mercuric oxide (Starplex Scientific, Inc., Etobicoke, Ontario, Canada) and thimerosal (Sigma Chemical Co., St. Louis, Mo.) effectively stabilize samples, their high National Fire Protection Association (NFPA) health hazard rating makes them unsuitable for use when large numbers of samples or high volumes of material are being processed. While sodium azide (Sigma Chemical Co.) is also an effective stabilizing material, the health rating assigned to sodium azide indicates that short exposure could cause serious temporary or residual health injury, making it unsuitable for use in high volume processing. While boric acid (Becton Dickinson, Franklin Lakes, N.J.) (Sage, Inc., Crystal Lakes, Ill.) (Bibby Sterlin, Ltd., Dynalab Corp., Rochester, N.Y.) and tartaric acid (Mid-America Health, Niagara Falls, N.Y.) have moderate to low NFPA hazard ratings, they are not cidal and, consequently, do not effectively block the deleterious effects of all microorganisms of interest, potentially causing false negative and false positive urinalysis results when the urine sample is held at room temperature beyond 8 hours. Therefore, as illustrated in the case of urine samples submitted for urinalysis, there is a continuing need for an effective transport system which provides stability of the chemical and physical properties of patient specimens and bodily fluids without exposing patients, healthcare professionals, and laboratory personnel to serious health hazards.

Biological reagents, some of which are often used in diagnostic testing procedures, are also susceptible to chemical and physical alteration due to microbial contamination. These reagents contain substances which are critical to their function but also capable of supporting microbial growth and/or metabolism. Although most biological reagents are manufactured under sterile conditions in sealed containers, low level microbial contamination can occur during manufacturing. During storage, the growth of the contaminating microorganisms can cause chemical and physical changes to the reagent. Moreover, many reagents are sold in multiple-entry containers at volumes which allow the user to repetitively extract small aliquots over time. There exists the possibility of microbial contamination of the reagent at each entry event. One commercially available preservative for reagents is Micr-O-protect™ (Roche Diagnostics, GmbH, Mannheim, Germany), an ethanolic solution of bromonitrodioxane and methylisothiazolone, with a health rating indicating that short exposure could cause serious temporary or residual injury and a flammability rating indicating that it could be ignited under most ambient conditions. Another preservative is the StabilZyme Select® Conjugate Stabilizer (SurModics, Inc., Eden Prairie, Minn.) which is an aqueous protein-containing mixture preserved with methylisothiazolone and bromonitrodioxane. Yet another line of preservative is ProClin (Supelco Inc., Bellefonte, Pa.) which utilizes 5-chloro-2-methyl-4-isothiazolin3-one and 2-methyl-4-isothiazolin-3-one. Isothiazolone and its derivatives are corrosive to the eyes potentially causing permanent irreversible injury, can cause skin burns or irritation, and are considered toxic to fish and wildlife if permitted to enter the water supply. Bromonitrodioxane is a formaldehyde releaser, and since formaldehyde is carcinogenic and highly flammable in liquid and gaseous forms, bromonitrodioxane is an unfavorable candidate as a preservative for samples processed in high volume. Consequently, there is a need for an environmentally friendly system which can preserve a biological reagent while maintaining its chemical and physical properties.

Preservatives are often added to therapeutics to increase shelf-life and to reduce the possibility of microbial contamination. As in the case of biological reagents, many therapeutics are packaged in multiple-entry containers at volumes which allow the extraction of small aliquots over time. For example, vaccines are routinely provided in multiple entry containers, and for several decades, thimerosal, a mercury-based preservative, has been used in vaccines to prevent contamination and other biologics in multidose containers. The Food and Drug Administration (FDA) has undertaken a review of drugs containing mercury-based preservatives, including thimerosal, in an effort to reduce the concentration of mercury in vaccines and to find alternative preservative formulations that do not contain mercury. ("Recommendations regarding the use of vaccines that contain thimerosal as a preservative," MMWR 48:996–998 Nov. 5, 1999)) Therefore, there is a need to provide safe, effective preservatives for therapeutics which reduce the risk of microbial contamination as well as potential health problems associated with exposure to mercury.

Microbial contamination can also lead to the chemical and/or physical degradation of personal care products such as cosmetics, hand cleansers, lotions, and shampoos. Moreover, contaminated products routinely exhibit diminished performance and contribute to the spread of infection to users.

Work surfaces and equipment in hospitals and laboratories are highly susceptible to microbial contamination. Likewise, surfaces and appliances found in kitchens and bathrooms of households, restaurants, groceries, catering establishments and the like are routinely exposed to microbial contamination. There is a continuing need for environmentally safe, effective sanitizing products capable of reducing the microbial bioburden in these areas as well.

SUMMARY OF THE INVENTION

In one aspect, the invention is a system for preserving a sample which may contain microorganisms, the system including an effective amount of a composition comprising a biguanide and at least one other antimicrobial agent, and the composition being cidal to the microorganisms when present in the sample and containing no antimicrobial additive having a National Fire Protection Association health hazard rating higher than moderate. In one embodiment, the biguanide utilized in the system is chlorhexidine. In another embodiment, the composition comprises a biguanide and at least one other antimicrobial agent comprising a compound that reduces the selective permeability of the cell membrane of the microorganisms. In another embodiment, the composition comprises chlorhexidine and at least one other antimicrobial agent comprising a compound that reduces the selective permeability of the cell membrane of the microorganisms. In another embodiment, the composition comprises a biguanide and an aromatic alcohol. In another embodiment, the composition comprises chiorhexidine and an aromatic alcohol. In another embodiment, the composition comprises a biguanide and 2-phenyl ethanol. In another embodiment, the composition comprises chlorhexidine and 2-phenyl ethanol. In another embodiment, the composition comprises a biguanide an aromatic alcohol, and a terpenoid. In another embodiment, the composition comprises chlorhexidine, an aromatic alcohol, and a terpenoid. In another embodiment, the composition comprises a biguanide, 2-phenyl ethanol, and a terpenoid. In another embodiment, the composition comprises chlorhexidine, 2-phenyl ethanol, and a terpenoid. In another embodiment, the composition comprises a biguanide, an aromatic alcohol, and isoeugenol. In another embodiment, the composition comprises chlorhexidine, an aromatic alcohol, and isoeugenol. In another embodiment, the composition comprises a biguanide, 2-phenyl ethanol, and isoeugenol. In another embodiment, the composition comprises chlorhexidine, 2-phenyl ethanol, and isoeugenol. In another embodiment, the composition comprises a biguanide and a propionate. In another embodiment, the composition comprises chlorhexidine and a propionate. In another embodiment, the composition comprises a biguanide and sodium propionate. In another embodiment, the composition comprises chlorhexidine and sodium propionate. In another embodiment, the composition comprises a biguanide, a propionate, and a parahydroxybenzoate. In another embodiment, the composition comprises chlorhexidine, a propionate, and a parahydroxybenzoate. In another embodiment, the composition comprises a biguanide, sodium propionate, and parahydroxybenzoate. In another embodiment, the composition comprises chlorhexidine, sodium propionate, and parahydroxybenzoate. In another embodiment, the composition comprises a biguanide, a propionate, and ethyl parahydroxybenzoate. In another embodiment, the composition comprises chlorhexidine, a propionate, and ethyl parahydroxybenzoate. In another embodiment, the composition comprises a biguanide, sodium propionate, and ethyl parahydroxybenzoate. In another embodiment, the composition comprises chlorhexidine, sodium propionate, and ethyl parahydroxybenzoate. In another embodiment, the composition comprises a biguanide and boric acid or a boric acid derivative. In another embodiment, the composition comprises chlorhexidine and boric acid or a boric acid derivative. In another embodiment, the composition comprises a biguanide, a propionate, and boric acid or a boric acid derivative. In another embodiment, the composition comprises chlorhexidine, a propionate, and boric acid or a boric acid derivative. In another embodiment, the composition comprises a biguanide, sodium propionate, and boric acid or a boric acid derivative. In another embodiment, the composition comprises chlorhexidine, sodium propionate, and boric acid or a boric acid derivative. The system is useful for samples selected from patient specimens, bodily fluids, reagents, therapeutics, personal care products and sanitizable surface.

In another aspect, the invention is a device comprising an accessible, sealable enclosure for containing and preserving a sample which may contain microorganisms, the enclosure containing a composition free of toxins including mercury, mercury containing compounds, formaldehyde, formaldehyde-releasing compounds, and azides which are unsuitable for use in high volume processing, and comprising a biguanide and at least one other antimicrobial agent, the composition being cidal to microorganisms when present in the sample. In one embodiment, the biguanide utilized in the system is chlorhexidine. In another embodiment, the composition comprises a biguanide and at least one other antimicrobial agent comprising a compound that reduces the selective permeability of the cell membrane of the microorganisms. In another embodiment, the composition comprises chlorhexidine and at least one other antimicrobial agent comprising a compound that reduces the selective permeability of the cell membrane of the microorganisms. In another embodiment, the composition comprises a biguanide and an aromatic alcohol. In another embodiment, the composition comprises chlorhexidine and an aromatic alcohol. In another embodiment, the composition comprises a biguanide and 2-phenyl ethanol. In another embodiment, the composition comprises chlorhexidine and 2-phenyl ethanol. In another embodiment, the composition comprises a biguanide an aromatic alcohol, and a terpenoid. In another embodiment, the composition comprises chlorhexidine, an aromatic alcohol, and a terpenoid. In another embodiment, the composition comprises a biguanide, 2-phenyl ethanol, and a terpenoid. In another embodiment, the composition comprises chiorhexidine, 2-phenyl ethanol, and a terpenoid. In another embodiment, the composition comprises a biguanide, an aromatic alcohol, and isoeugenol. In another embodiment, the composition comprises chlorhexidine, an aromatic alcohol, and isoeugenol. In another embodiment, the composition comprises a biguanide, 2-phenyl ethanol, and isoeugenol. In another embodiment, the composition comprises chiorhexidine, 2-phenyl ethanol, and isoeugenol. In another embodiment, the composition comprises a biguanide and a propionate. In another embodiment, the composition comprises chiorhexidine and a propionate. In another embodiment, the composition comprises a biguanide and sodium propionate. In another embodiment, the composition comprises chlorhexidine and sodium propionate. In another embodiment, the composition comprises a biguanide, a propionate, and a parahydroxybenzoate. In another embodiment, the composition comprises chlorhexidine, a propionate, and a parahydroxybenzoate. In another embodiment, the composition comprises a biguanide, sodium propionate, and parahydroxybenzoate. In another embodiment, the composition comprises chlorhexidine, sodium propionate, and parahydroxybenzoate. In another embodiment, the composition comprises a biguanide, a propionate, and ethyl parahydroxybenzoate. In another embodiment, the composition comprises chlorhexidine, a propionate, and ethyl parahydroxybenzoate. In another embodiment, the composition comprises a biguanide, sodium propionate, and ethyl parahydroxybenzoate. In another embodiment, the composition comprises chlorhexidine, sodium propionate, and ethyl parahydroxybenzoate. In another embodiment, the composition comprises a biguanide and boric acid or a boric acid derivative. In another embodiment, the composition comprises chlorhexidine and boric acid or a boric acid derivative. In another embodiment, the composition comprises a biguanide, a propionate, and boric acid or a boric acid derivative. In another embodiment, the composition comprises chlorhexidine, a propionate, and boric acid or a boric acid derivative. In another embodiment, the composition comprises a biguanide, sodium propionate, and boric acid or a boric acid derivative. In another embodiment, the composition comprises chlorhexidine, sodium propionate, and boric acid or a boric acid derivative. The device is useful for samples selected from patient specimens, bodily fluids, reagents, therapeutics, and personal care products.

In another aspect, the invention is an improved method for preserving a sample which may contain microorganisms, the improvement comprising preserving the chemical and physical properties of the sample by mixing the sample with an effective amount of a composition comprising a biguanide and at least one other antimicrobial agent, wherein the composition is cidal to microorganisms when present in the sample. In one embodiment, the biguanide utilized in the system is chlorhexidine. In another embodiment, the composition comprises a biguanide and at least one other antimicrobial agent comprising a compound that reduces the selective permeability of the cell membrane of the microorganisms. In another embodiment, the composition comprises chlorhexidine and at least one other antimicrobial agent comprising a compound that reduces the selective permeability of the cell membrane of the microorganisms. In another embodiment, the composition comprises a biguanide and an aromatic alcohol. In another embodiment, the composition comprises chlorhexidine and an aromatic alcohol. In another embodiment, the composition comprises a biguanide and 2 phenyl ethanol. In another embodiment, the composition comprises chlorhexidine and 2 phenyl ethanol. In another embodiment, the composition comprises a biguanide an aromatic alcohol, and a terpenoid. In another embodiment, the composition comprises chlorhexidine, an aromatic alcohol, and a terpenoid. In another embodiment, the composition comprises a biguanide, 2-phenyl ethanol, and a terpenoid. In another embodiment, the composition comprises chlorhexidine, 2-phenyl ethanol, and a terpenoid. In another embodiment, the composition comprises a biguanide, an aromatic alcohol, and isoeugenol. In another embodiment, the composition comprises chlorhexidine, an aromatic alcohol, and isoeugenol. In another embodiment, the composition comprises a biguanide, 2-phenyl ethanol, and isoeugenol. In another embodiment, the composition comprises chlorhexidine, 2-phenyl ethanol, and isoeugenol. In another embodiment, the composition comprises a biguanide and a propionate. In another embodiment, the composition comprises chlorhexidine and a propionate. In another embodiment, the composition comprises a biguanide and sodium propionate. In another embodiment, the composition comprises chlorhexidine and sodium propionate. In another embodiment, the composition comprises a biguanide, a propionate, and a parahydroxybenzoate. In another embodiment, the composition comprises chlorhexidine, a propionate, and a parahydroxybenzoate. In another embodiment, the composition comprises a biguanide, sodium propionate, and parahydroxybenzoate. In another embodiment, the composition comprises chlorhexidine, sodium propionate, and parahydroxybenzoate. In another embodiment, the composition comprises a biguanide, a propionate, and ethyl parahydroxybenzoate. In another embodiment, the composition comprises chlorhexidine, a propionate, and ethyl parahydroxybenzoate. In another embodiment, the composition comprises a biguanide, sodium propionate, and ethyl parahydroxybenzoate. In another embodiment, the composition comprises chlorhexidine, sodium propionate, and ethyl parahydroxybenzoate. In another embodiment, the composition comprises a biguanide and boric acid or a boric acid derivative. In another embodiment, the composition comprises chlorhexidine and boric acid or a boric acid derivative. In another embodiment, the composition comprises a biguanide, a propionate, and boric acid or a boric acid derivative. In another embodiment, the composition comprises chlorhexidine, a propionate, and boric acid or a boric acid derivative. In another embodiment, the composition comprises a biguanide, sodium propionate, and boric acid or a boric acid derivative. In another embodiment, the composition comprises chlorhexidine, sodium propionate, and boric acid or a boric acid derivative. The device is useful for samples selected from patient specimens, bodily fluids, reagents, therapeutics, and personal care products.

DETAILED DESCRIPTION

A transport/preservative system has been found which provides safe, effective transport for patient specimens and bodily fluids, and functions as a preservative for biological reagents, therapeutics, and personal care products. The transport/preservative formulations can also be used as safe, effective sanitizers on surfaces, equipment, and appliances.

In describing the features of the transport/preservative system of the present invention, the following terms are defined as given below. The term "cidal" is defined as having antimicrobial activity against gram positive and gram negative bacteria and yeasts, wherein the effective antimicrobial strength is sufficient to cause a reduction of at least 2–3 logs in organism count within 24 hours or to cause sufficient damage to the microorganisms present so that their metabolism is arrested to a level at which the microorganisms cannot alter the chemical or physical properties of the sample. Unless otherwise stated, the term "sample" refers to either a diagnostic or laboratory sample, bodily fluid, biological reagent, personal care product, or therapeutic. The term "therapeutic" includes topically, subcutaneously, intramuscularly, orally, mucosally, and unguinally administered pharmaceuticals, nutraceuticals, and over-the-counter preparations.

The transport/preservative system of the present invention utilizes antimicrobial agents having low environmental impact to synergistically provide microbiocidal activity. The transport/preservative system of the present invention provides cidal, not static, antimicrobial activity against the majority of microorganisms commonly found in diagnostic samples, biological reagents, personal care products, or therapeutics, thereby effectively reducing the microbial count to levels which will not cause chemical or physical degradation for extended periods of time at room temperature. Use of the transport/preservative system of the present invention does not alter the chemical properties of interest of the sample. For example, the amount of glucose, ketone, protein, urobilinogen, nitrite, and blood in a patient urine sample can be maintained for extended periods of time. Likewise, the transport/preservative system of the present invention does not alter the physical properties of interest of the sample, e.g., presence of leukocytes, cast cells or red blood cells, specific gravity, color, pH, or buffering capacity of a sample. If desired, the morphological integrity of killed microorganisms in samples can be preserved for over 72 hours, thus allowing meaningful microscopic analysis. The major components of the transport/preservative formulations of the present invention which provide its antimicrobial action are shelf-stable and have a moderate to low NFPA hazard rating indicative of environmental safety. The transport/preservative system of the present invention utilizes combinations of at least two antimicrobial components to achieve cidal action against microorganisms while maintaining the chemical and physical integrity of the sample, thus reducing the possibility of the development of resistance in the microorganisms of interest to one particular antimicrobial component. Additionally, the antimicrobial components of the transport/preservative system act synergistically to permit the use of lower effective concentrations of each component, thereby reducing any possible deleterious effects of individual components on the chemical and physical properties of the sample as well as limiting the exposure of patients, healthcare professionals, laboratory personnel, and consumers to the components. The antimicrobial action of the transport/preservative formulations is also sufficient to sanitize surfaces, containers, equipment, appliances and the like. The variety of transport/preservative formulations presented herein include formulations which are compatible with glass, plastic, rubber, and metal, thus permitting use of the transport/preservative system with a wide range of surfaces, containers, device formats, and instrumentation.

The transport/preservative system of the present invention comprises at least two antimicrobial components. By using more than one antimicrobial component, the transport/preservative system increases the probability of controlling the growth and/or metabolism of potentially resistant microorganisms. The effective combination of antimicrobial components must be cidal. For patient samples which require microscopic examination, e.g., urine specimens, the antimicrobial components of the transport/preservative system of the present invention can be selected to preserve gross cellular morphology.

The antimicrobial components of the present invention must be soluble and chemically stable at room temperature in aqueous solutions at effective concentrations. Another characteristic of the antimicrobial components is that, at effective concentrations, they cannot possess sufficient acidity, basicity, or buffering capacity so as to alter the pH of the sample. The antimicrobial components must be stable and effective through a broad pH range, i.e, from about pH 4 to about pH 8. For samples where specific gravity is considered an important parameter, e.g., urine samples, the specific gravity of the antimicrobial components in aqueous solution must be sufficiently similar to water so as to not change the specific gravity of the sample.

Antimicrobial biguanides are one important class of compounds used in the present invention. Among the useful biguanides are chlorhexidine and its derivatives (e.g., chlorhexidine gluconate), the alexidine group, and polymeric biguanides (e.g., polyhexamethylene biguanides). The preferred biguanides are chlorhexidine and its derivatives. It is understood that similar biguanides with bromide and/or iodide ions substituted for the chloride ions can be used in the present invention.

Antimicrobial agents which damage the cell membrane of microorganisms and subsequently reduces or destroys the cell membrane's selective permeability are also important components of the present invention. These include but are not limited to antimicrobial aromatic alcohols, terpenoids, parahydroxybenzoate esters, deoxycholates, taurocholates, and detergents/surfactants. Suitable antimicrobial aromatic alcohols include but are not limited to phenylethyl alcohol, benzyl alcohol, and phenoxyethyl alcohol. Preferred terpenoids include but are not limited to isoeugenol, isohexanol, and isooctanol. Suitable parahydroxybenzoate esters include but are not limited to alkyl esters such as methyl-, ethyl-, propyl-, and butyl-parahydroxybenzoates as well as the aromatic benzylparahydroxybenzoate. Preferred detergents/surfactants are lipid-active such as octoxynol (Triton-X).

Antimicrobial organic acids are another important class of antimicrobial components of the present invention. Preferred organic acids include but are not limited to acetic, propionic, benzoic, citrate, and sorbic acid and their monvalent salts. In urine transport, ammonium salts are not useful due to their interference in routine diagnostics tests. Most preferred is sodium propionate.

Boric acid and its derivatives are other important antimicrobial components of the present invention. Unlike commercially available specimen transport systems using boric acid to provide microbial stasis, the transport/preservative system of the present invention uses boric acid in combination with other antimicrobial components to provide microbial cidal action.

Optionally, the transport/preservative system of the present invention can comprise fragrance components. Preferably, the fragrance components are antimicrobial. Preferred fragrance components include but are not limited to isoeugenol, ethyl vanillin, and pinacol.

A preferred stabilizing, transport/preservative formulation of the present invention comprises an antimicrobial aromatic alcohol, an alkyl guaiacol, and a biguanide. One example of this formulation, hereinafter referred to as "Chemistat I," comprises 2-phenyl ethanol, isoeugenol, and chlorhexidine. Most preferably, Chemistat I formulations comprise 2-phenyl ethanol from about 0 $\mu$l/ml to about 2.5 $\mu$l/ml, isoeugenol from about 0.2 $\mu$l/ml to about 1.5 $\mu$l/ml, and chlorhexidine from about 0.01 mg/ml to about 0.1 mg/ml, and any combination thereof. These concentrations and subsequent concentrations for the transport/preservative system reported herein are the final concentration after the sample is added. To preserve urine specimens, the Chemistat I formulation preferably comprises 2-phenyl ethanol at about 1.8 $\mu$l/ml, isoeugenol at about 0.2 $\mu$l/ml, and chlorhexidine at about 0.02 mg/ml. The Chemistat I formulations are in liquid form, and 2-phenyl ethanol, isoeugenol, and chlorhexidine are all active ingredients. Additionally, 2-phenyl ethanol and isoeugenol provide a synthetic rose scent and a spicy fragrance, respectively, to mask sample odor.

EXAMPLE 1

Effectiveness of Chemistat I Formulations

Chemistat I formulations were shown to preserve urine samples containing significant microbial contamination and at the same time maintain the chemical and physical properties of the urine samples.

Antimicrobial activity for each active ingredient in the Chemistat I formulations was first determined for representative organisms listed in Table I. A culture for each organism of interest on blood agar was incubated at 36° C. overnight. About two to three colonies of the organism were transferred via sterile swab from the blood agar culture into a 5 ml Mueller-Hinton broth culture tube, which was then incubated on a rotator for about two to three hours at 36° C. Using a spectrophotometer set at a wavelength of 630 nm, the turbidity of broth culture was adjusted by the addition of Mueller-Hinton broth to an optical density equivalent to approximately $1\times10^8$ colony forming units (cfu)/ml to form an inoculum solution. An aliquot of the inoculum solution was plated onto blood agar to determine the actual control organism count. For each component listed in Table II, the component was added to filter-sterilized pooled normal urine at the concentration given in Table II to form a test sample. The test sample was then inoculated with an aliquot of the inoculum solution providing a final organism count of approximately $1\times10^6$ cfu/ml of test sample. Immediately after thorough mixing, an aliquot of the test sample was removed and serially diluted in PBS, and serial dilutions were plated onto blood agar to determine the Time Zero organism count. The inoculated plates were incubated at 36° C., and organism counts were recorded after 18–24 hours. After incubating the test sample for 24 hours at room temperature, an aliquot of the test sample was again removed, serially diluted in PBS and plated onto blood agar. After incubating for 18–24 hours at 36° C., organism counts were obtained. The organism count obtained after 24 hours incubation at room temperature was divided by the control organism count to provide the survival value of each organism as recorded in Table II. With respect to changes in microbial count, a survival value of 1 represents no change; a survival value of 0.1 indicates a 1-log decrease; a survival value of 10 indicates a 1-log increase; and a survival value of 0.000 represents a decrease of greater than or equal to 3-logs. In comparison, the lower the survival value, the greater the component's capacity for controlling organism growth.

As shown in Table II, 2-phenyl ethanol alone exhibited cidal activity against *Escherichia coli* at 4 $\mu$l/ml; *Pseudomonas aeruginosa*, at 5 $\mu$l/ml; *Enterobacter aerogenes* and *Candida albicans*, at 10 $\mu$l/ml; but was not cidal against *Enterococcus faecalis* at up to 10 $\mu$l/ml. Further, 2-phenyl ethanol produced a strong unpleasant odor when combined with urine at concentrations of 4–10 $\mu$l/ml, making it undesirable for use as a urine preservative at these concentrations. Isoeugenol showed cidal activity against *Escherichia coli* at 1.5 $\mu$l/ml; *Candida albicans* and *Enterobacter aerogenes*, at 2.5 $\mu$l/ml; but was not cidal against *Enterococcus faecalis* at up to 4.6 $\mu$l/ml. Chlorhexidine had cidal activity against *Escherichia coli* and *Candida albicans* at 0.0075 mg/ml; *Enterobacter aerogenes*, at 0.01 mg/ml; *Proteus vulgaris* and *Klebsiella pneumoniae*, at 0.02 mg/ml; showed variable cidal activity against *Enterococcus faecalis* at 0.05–0.8 mg/ml; and was not cidal against *Pseudomonas aeruginosa at up to* 0.05 mg/ml. In summary, the three active ingredients each had cidal activity against some but not all of the microorganisms of interest. Cidal antimicrobial action for many organisms of interest with isoeugenol alone required a concentration greater than 1.5 µl/ml; cidal action with 2-phenyl ethanol alone required a concentration greater than 2.5 µl/ml; cidal action with chlorhexidine required a concentration of greater than or equal to 0.01 mg/ml.

TABLE I

List of Organisms Used

| Organism Name | Code | Ref. Number |
|---|---|---|
| *Acinetabacter calcoaceticus* | acca1 | 14290[a] |
|  | acca2 | 23055[a] |
| *Alcaligenes faecalis* | alfa1 | 8750[a] |
|  | alfa2 | 35655[a] |
| *Candida albicans* | caal1 | 14053[a] |
|  | caal2 | 60193[a] |
| *Citrobacter diversus* | cidi1 | 29225[a] |
|  | cidi2 | 3220-2[a] |
| *Citrobacter freundii* | cifr1 | 33128[a] |
|  | cifr2 | 699[b] |
| *Enterobacter aerogenes* | enae1 | 13048[a] |
|  | enae2 | 2490[b] |
| *Enterobacter cloacae* | encl1 | 29006[a] |
|  | encl2 | 31181[b] |
| *Enterocaccus faecalis* | enfa1 | 29212[a] |
|  | enfa2 | 49477[a] |
| *Escherichia coli* | esco1 | 25922[a] |
|  | esco2 | 11303[a] |

TABLE I-continued

List of Organisms Used

| Organism Name | Code | Ref. Number |
|---|---|---|
|  | esco3 | 29194[a] |
|  | esco4 | 8739-1[b] |
| *Klebsiella oxytoca* | klox1 | 43165[a] |
|  | klox2 | 33496[a] |
| *Klebsiella pneumoniae* | klpn1 | 33495[a] |
|  | klpn2 | 13883[a] |
| *Morganella morganii* | momo1 | 25830[a] |
|  | momo2 | 29853[a] |
| *Proteus mirabilis* | prmi1 | 7002[a] |
|  | prmi2 | 12453[a] |
| *Proteus vulgaris* | prvu1 | 13315[a] |
|  | prvu2 | 49132[a] |
| *Providencia stuartii* | prst1 | 29914[a] |
|  | prst2 | 49809[a] |
| *Pseudomonas aeruginosa* | psae1 | 27853[a] |
|  | psae2 | 10145[a] |
| *Serratia marcescens* | sema1 | 9103[a] |
|  | sema2 | 3155[b] |
| *Staphylacoccus aureus* | stau1 | 25923[a] |
|  | stau2 | 33591[a] |
| *Strepococcus agalactiae* | stag1 | 624[a] |
|  | stag2 | 13813[a] |

[a]Strains obtained from the American Type Culture Collection (ATCC).
[b]Strains obtained from patient samples and identified by routine clinical microbiology tests.

TABLE II

Antimicrobial Activity for Individual Chemistat I Components

Survival Values[a] after 24 hours at Room Temperature for Representative Organisms[b]

| Component | esco | psae | prvu | enfa | caal | klpn | enae |
|---|---|---|---|---|---|---|---|
| 2-Phenyl ethanol (1 µl/ml) | tntc | 4.819 |  | tntc |  |  | tntc |
| 2-Phenyl ethanol (1.8 µl/ml) | tntc | tntc | tntc | tntc | tntc | tntc |  |
| 2-Phenyl ethanol (2.5 µl/ml) | 0.245 | 0.199 |  | tntc |  |  | 0.092 |
| 2-Phenyl ethanol (4 µl/ml)[c] | 0.000 | 0.019 |  | tntc | 1.081 |  | 0.244 |
| 2-Phenyl ethanol (5 µl/ml)[c] |  | 0.000 |  | tntc |  |  | 0.440 |
| 2-Phenyl ethanol (10 µl/ml)[c] | 0.000 | 0.000 |  | 1.495 | 0.000 |  | 0.000 |
| Chlorhexidine (0.005 mg/ml) | 0.003 | tntc |  | 1.115 | 5.308 |  | tntc |
| Chlorhexidine (0.0075 mg/ml) | 0.000 | 4.049 |  | 0.598 | 0.000 |  | 6.098 |
| Chlorhexidine (0.01 mg/ml) | 0.000 | 0.277 |  | 0.520 |  |  | 0.000 |
| Chlorhexidine (0.02 mg/ml) | 0.000 | 0.275 | 0.000 | 0.179 |  |  |  |
| Chlorhexidine (0.02 mg/ml) | 0.000 | 0.080 | 0.000 | 0.141 | 0.000 | 0.000 |  |
| Chlorhexidine (0.05 mg/ml) | 0.000 | 0.046 |  | 0.000 | 0.000 |  | 0.000 |
| Chlorhexidine (0.1 mg/ml) | 0.000 |  |  | 0.561 | 0.000 |  |  |
| Chlorhexidine (0.8 mg/ml)[d] | 0.000 |  |  | 0.000 | 0.000 |  |  |
| Isoeugenol (0.2 µl/ml) | tntc | tntc | tntc | tntc | 0.160 | tntc |  |
| Isoeugenol (0.5 µl/ml) | tntc |  |  | tntc | 2.786 |  |  |
| Isoeugenol (1.5 µl/ml) | 0.000 | tntc |  | tntc | 0.152 |  | tntc |

TABLE II-continued

Antimicrobial Activity for Individual Chemistat I Components

| Component | Survival Values[a] after 24 hours at Room Temperature for Representative Organisms[b] | | | | | | |
|---|---|---|---|---|---|---|---|
| | esco | psae | prvu | enfa | caal | klpn | enae |
| Isoeugenol (2.5 µl/ml)[c] | 0.000 | 0.398 | | 0.750 | 0.000 | | 0.000 |
| Isoeugenol (4.6 µl/ml)[c] | 0.000 | | | 0.460 | 0.000 | | |

[a]Numbers indicate survival values (number of organisms recovered after 24 hours incubation at room temperature divided by the initial control count; tntc = organisms at 24 hours too numerous to count.
[b]Organism Key: esco = *Escherichia coli*; psae = *Pseudomonas aeruginosa*; prvu = *Proteus vulgaris*; enfa = *Enterococcus faecalis*; caal = *Candida albicans*; klpn = *Klebsiella pneumoniae*; enae = *Enterobacter aerogenes*.
[c]Strong unpleasant odor.
[d]Produced a false positive protein upon urinalysis.

As shown in Table III, the components of the Chemistat I formulations of the present invention act synergistically with each other, in that the effective concentration of each individual component of the formulation necessary for cidal action against the microorganisms of interest is less than the effective concentration of each component tested separately, and also a wider range of microorganisms are killed with the formulation. For example, neither isoeugenol at 1.5 µl/ml nor chlorhexidine at 0.005 mg/ml alone are cidal against *Candida albicans, Pseudomonas aeruginosa,* or *Enterobacter aerogenes,* but the combination is cidal against *Candida albicans* and *Enterobacter aerogenes* and inhibitory against *Pseudomonas aeruginosa*. Isoeugenol at 0.2 µl/ml was not cidal against any of the organisms of interest and chlorhexidine at 0.02 mg/ml was not cidal against *Pseudomonas aeruginosa* and *Enterococcus faecalis*; however, the combination was cidal against all organisms of interest given in Table III. Neither isoeugenol at 0.2 µl/ml nor 2-phenyl ethanol at 1.8 µl/ml had any effect against *Escherichia coli* when used alone, but when used together, they inhibited *Escherichia coli*. Chlorhexidine at 0.02 mg/ml was not cidal against *Pseudomonas aeruginosa* and *Enterococcus faecalis*, and 2-phenyl ethanol at 1.8 µl/ml did not inhibit any organism of interest. However, the combination of chlorhexidine (0.02 mg/ml) and 2-phenyl ethanol (1.8 µl/ml) was cidal against all organisms of interest in Table III. Extensive studies using all of the organisms listed in Table I showed that Chemistat I formulations stabilize urine samples initially containing approximately $1\times10^6$ cfu/ml for a period of seven days at room temperature (22–25° C.). (Data not shown) It is anticipated that other fragrances such as ethyl vanillin (2 mg/ml) or pinacol (10 mg/ml) can be added to Chemistat I formulations, e.g., a combination of isoeugenol (0.2 µl/ml) and chlorhexidine (0.02 mg/ml) to produce a cidal transport/preservative system.

TABLE III

Antimicrobial Activity for Chemistat I Component Combinations

| Component Combinations | Survival Values[a] after 24 hours at Room Temperature for Representative Organisms[b] | | | | | | |
|---|---|---|---|---|---|---|---|
| | esco | psae | prvu | enfa | caal | klpn | enae |
| Isoeugenol (1.5 µl/ml); chlorhexidine (0.005 mg/ml) | 0.000 | 0.032 | | 0.780 | 0.000 | | 0.000 |
| 2-Phenyl ethanol (5 µl/ml); chlorhexidine (0.1 mg/ml)[c] | 0.000 | 0.000 | | 0.000 | | | 0.000 |
| 2-Phenyl ethanol (5 µl/ml); chlorhexidine (0.01 mg/ml)[c] | 0.000 | 0.000 | | 0.023 | 0.000 | | 0.000 |
| 2-Phenyl ethanol (2.5 µl/ml); chlorhexidine (0.005 mg/ml) | 0.000 | 0.136 | | 0.730 | 0.757 | | 0.000 |
| 2-Phenyl ethanol (1.25 µl/ml); chlorhexidine (0.0025 mg/ml) | 0.000 | tntc | | 1.157 | 2.748 | | 0.988 |
| 2-Phenyl ethanol (4 µl/ml); chlorhexidine (0.0075 mg/ml)[c] | 0.000 | 0.000 | | 0.128 | 0.000 | | 0.000 |
| 2-Phenyl ethanol (1.8 µl/ml); isoeugenol (0.2 µl/ml) | 0.147 | tntc | | tntc | 0.306 | | tntc |
| 2-Phenyl ethanol (1.8 µl/ml); isoeugenol (0.2 µl/ml); chlorhexidine (0.005 mg/ml) | 0.000 | 0.000 | | 0.214 | 0.121 | | 0.000 |
| 2-Phenyl ethanol (1.8 µl/ml); isoeugenol (0.2 µl/ml); chlorhexidine (0.01 mg/ml) | 0.000 | 0.000 | | 0.075 | 0.000 | | 0.000 |
| 2-Phenyl ethanol (3.8 µl/ml); isoeugenol (0.2 µl/ml)[c] | 0.000 | 0.105 | | tntc | 0.758 | | 0.000 |
| 2-Phenyl ethanol (3.8 µl/ml); isoeugenol (0.2 µl/ml); chlorhexidine (0.005 mg/ml)[c] | 0.000 | 0.000 | | 0.000 | 0.185 | | 0.000 |

TABLE III-continued

Antimicrobial Activity for Chemistat I Component Combinations

| Component Combinations | Survival Values[a] after 24 hours at Room Temperature for Representative Organisms[b] | | | | | | |
|---|---|---|---|---|---|---|---|
| | esco | psae | prvu | enfa | caal | klpn | enae |
| 2-Phenyl ethanol (3.8 μl/ml); isoeugenol (0.2 μl/ml); chlorhexidine (0.01 mg/ml)[c] | 0.000 | 0.000 | | 0.000 | 0.000 | | 0.094 |
| 2-Phenyl ethanol (1.8 μl/ml); isoeugenol (0.2 μl/ml) | 0.487 | tntc | 1.315 | tntc | 0.136 | tntc | |
| 2-Phenyl ethanol (1.8 μl/ml); chlorhexidine (0.02 mg/ml) | 0.000 | 0.000 | 0.000 | 0.000 | 0.000 | 0.000 | |
| Isoeugenol (0.2 μl/ml); chlorhexidine (0.02 mg/ml) | 0.000 | 0.000 | 0.000 | 0.000 | 0.000 | 0.000 | |
| 2-Phenyl ethanol (1.8 μl/ml); chlorhexidine (0.02 mg/ml); isoeugenol (0.2 μl/ml) | 0.000 | 0.000 | 0.000 | 0.000 | 0.000 | 0.000 | |

[a]Numbers indicate survival values (number of organisms recovered after 24 hours incubation at room temperature divided by the initial control count; tntc = organisms at 24 hours too numerous to count.
[b]Organism Key: esco = *Escherichia coli*; psae = *Pseudomonas aeruginosa*; prvu = *Proteus vulgaris*; enfa = *Enterococcus faecalis*; caal = *Candida albicans*; klpn = *Klebsiella pneumoniae*; enae = *Enterobacter aerogenes*.
[c]Strong unpleasant odor.

With respect to urinalysis, the components of the Chemistat I formulations at their preferred concentrations did not affect any urinalysis parameter or microbial morphology when normal pooled urine was inoculated with microorganisms of interest at $1 \times 10^6$ cfu/ml. However, chlorhexidine at higher concentrations of greater than or equal to 0.8 mg/ml caused false positive protein readings.

Because of possible deleterious interactions of the Chemistat I formulation with plastics and possibly with the rubber stoppers and/or silicone commonly used in packaging, transport and/or processing containers, stabilizing transport/preservative formulations in powder, liquid, or lyophilized form which are inert to plastics, rubber, and silicone, hereinafter referred to as "Chemistat II", have been found, comprising an antimicrobial organic acid, an antimicrobial agent which attacks or disrupts the lipid membrane of microorganisms of interest, and antimicrobial biguanide. Preferably, Chemistat II comprises an antimicrobial proprionate, parahydroxy benzoate, and a biguanide. Most preferably, Chemistat II comprises sodium propionate, ethyl parahydroxybenzoate, and chlorhexidine. Preferred Chemistat II formulations comprise from about 1 mg/ml to about 10 mg/ml sodium proprionate, from about 0.1 mg/ml to about 1 mg/ml ethyl parahydroxybenzoate, and from about 0.01 mg/ml to about 0.1 mg/ml chlorhexidine, and any combination thereof. For preservation of urine specimens, a preferred Chemistat II formulation comprises 6 mg/ml sodium proprionate, 0.5 mg/ml ethyl parahydroxybenzoate, and 0.025 mg/ml chlorhexidine. Another preferred Chemistat II formulation for urine specimens comprises 6.25 mg/ml sodium propionate, 0.25 mg/ml ethyl parahydroxybenzoate, and 0.0275 mg/ml chlorhexidine.

EXAMPLE 2

Effectiveness of Chemistat II Formulations

Chemistat II formulations were shown to preserve urine samples containing significant microbial contamination and at the same time maintain the chemical and physical properties of the urine samples.

The antimicrobial results for the individual components are given in Table IV. As previously discussed, chlorhexidine alone had cidal activity against *Escherichia coli* and *Candida albicans* at 0.0075 mg/ml; *Enterobacter aerogenes*, at 0.01 mg/ml; *Proteus vulgaris* and *Klebsiella pneumoniae*, at 0.02 mg/ml; showed variable cidal activity against *Enterococcus faecalis* at 0.05–0.8 mg/ml; and was not cidal against *Pseudomonas aeruginosa* 10 at up to 0.05 mg/ml. Ethyl parahydroxybenzoate was cidal against *Escherichia coli* at 1 mg/ml; inhibitory against *Candida albicans* and *Enterobacter aerogenes*, at 0.5 mg/ml and 1 mg/ml, respectively; and ineffective against *Pseudomonas aeruginosa, Proteus vulgaris, Enterococcus faecalis*, and *Klebsiella pneumoniae* at up to 1 mg/ml. Sodium propionate was inhibitory against *Pseudomonas aeruginosa* and *Enterococcus faecalis* at 10 mg/ml, but was ineffective against *Escherichia coli, Proteus vulgaris, Candida albicans, Klebsiella pneumoniae*, and *Enterobacter aerogenes* at up to 10 mg/ml. Thus, the components of the Chemistat II formulations when used alone were unable to control the growth of the microorganisms of interest.

TABLE IV

Antimicrobial Activity for Individual Chemistat II Components

| Component | Survival Values[a] after 24 hours at Room Temperature for Representative Organisms[b] | | | | | | |
|---|---|---|---|---|---|---|---|
| | esco | psae | prvu | enfa | caal | klpn | enae |
| Chlorhexidine (0.005 mg/ml) | 0.003 | tntc | | 1.115 | 5.308 | | tntc |
| Chlorhexidine (0.0075 mg/ml) | 0.000 | 4.049 | | 0.598 | 0.000 | | 6.098 |

TABLE IV-continued

Antimicrobial Activity for Individual Chemistat II Components

| Component | Survival Values[a] after 24 hours at Room Temperature for Representative Organisms[b] | | | | | | |
|---|---|---|---|---|---|---|---|
| | esco | psae | prvu | enfa | caal | klpn | enae |
| Chlorhexidine (0.01 mg/ml) | 0.000 | 0.277 | | 0.520 | | | 0.000 |
| Chlorhexidine (0.02 mg/ml) | 0.000 | 0.275 | 0.000 | 0.179 | | | |
| Chlorhexidine (0.02 mg/ml) | 0.000 | 0.080 | 0.000 | 0.141 | 0.000 | 0.000 | |
| Chlorhexidine (0.05 mg/ml) | 0.000 | 0.046 | | 0.000 | 0.000 | | 0.000 |
| Chlorhexidine (0.1 mg/ml) | 0.000 | | | 0.561 | 0.000 | | |
| Chlorhexidine (0.8 mg/ml)[c] | 0.000 | | | 0.000 | 0.000 | | |
| Ethyl parahydroxybenzoate (0.5 mg/ml)[d] | tntc | tntc | tntc | tntc | 0.362 | tntc | |
| Ethyl parahydroxybenzoate (1 mg/ml)[d] | 0.000 | tntc | | tntc | | | 0.208 |
| Sodium propionate (5 mg/ml) | tntc | tntc | tntc | tntc | tntc | tntc | |
| Sodium propionate (10 mg/ml) | tntc | 0.341 | | 2.702 | | | |

[a]Numbers indicate survival values (number of organisms recovered after 24 hours incubation at room temperature divided by the initial control count; tntc = organisms at 24 hours too numerous to count.
[b]Organism Key: esco = *Escherichia coli*; psae = *Pseudomonas aeruginosa*; prvu = *Proteus vulgaris*; enfa = *Enterococcus faecalis*; caal = *Candida albicans*; klpn = *Klebsiella pneumoniae*; enae = *Enterobacter aerogenes*.
[c]Produced a false positive protein upon urinalysis.
[d]Low solubility in urine.

As shown in Table V, combinations of any two of the three Chemistat II components were not cidal for all microorganisms of interest, in particular, *Pseudomonas aeruginosa* and *Enterococcus faecalis*, at 24 hours. However, the combination of chlorhexidine at 0.02 mg/ml, sodium propionate at 5 mg/ml, and ethyl parahydroxybenzoate at 0.5 mg/ml was cidal for the organisms of interest. Further, the components of the Chemistat II formulations act synergistically with each other, in that the effective concentration of each individual component of the composition necessary for cidal action against the microorganisms of interest is less than the effective concentration of each component tested separately, and also a wider range of microorganisms are killed with the composition. For example, chlorhexidine (0.02 mg/ml) alone inhibits but does not kill *P. aeruginosa*, and ethyl parahydroxybenzoate (0.5 mg/ml) and sodium propionate (5 mg/ml) together do not affect this organism at all. However, when chlorhexidine, ethyl parahydroxybenzoate, and sodium proprionate are added together, the composition of the present invention is cidal against *P. aeruginosa*.

TABLE V

Antimicrobial Activity for Chemistat II Component Combinations

| Component Combinations | Survival Values[a] after 24 hours at Room Temperature for Representative Organisms[b] | | | | | |
|---|---|---|---|---|---|---|
| | esco | psae | prvu | enfa | caal | klpn |
| Chlorhexidine (0.02 mg/ml); sodium propionate (10 mg/ml) | 0.000 | 0.005 | 0.000 | 0.448 | | |
| Chlorhexidine (0.02 mg/ml); sodium propionate (5 mg/ml); ethyl parahydroxybenzoate (0.5 mg/ml) | | 0.000 | | 0.000 | | 0.000 |
| Chlorhexidine (0.02 mg/ml); sodium propionate (5 mg/ml); ethyl parahydroxybenzoate (0.3 mg/ml) | | 0.026 | | 0.010 | | |
| Chlorhexidine (0.02 mg/ml); sodium propionate (5 mg/ml); ethyl parahydroxybenzoate (0.1 mg/ml) | | 0.468 | | 0.155 | | |
| Ethyl parahydroxybenzoate (0.5 mg/ml); sodium propionate (5 mg/ml) | tntc | tntc | tntc | tntc | 0.523 | tntc |
| Ethyl parahydroxybenzoate (0.5 mg/ml); chlorhexidine (0.02 mg/ml) | 0.000 | 0.002 | 0.000 | 0.000 | 0.000 | 0.000 |
| Sodium propionate (5 mg/ml); chlorhexidine (0.02 mg/ml) | 0.000 | 0.326 | 0.000 | 0.605 | 0.000 | 0.000 |
| Ethyl parahydroxybenzoate (0.5 mg/ml); chlorhexidine (0.02 mg/ml); sodium proprionate (5 mg/ml) | 0.000 | 0.000 | 0.000 | 0.014 | 0.000 | 0.000 |

[a]Numbers indicate survival values (number of organisms recovered after 24 hours incubation at room temperature divided by the initial control count; tntc = organisms at 24 hours too numerous to count.
[b]Organism Key: esco = *Escherichia coli*; psae = *Pseudomonas aeruginosa*; prvu = *Proteus vulgaris*; enfa = *Enterococcus faecalis*; caal = *Candida albicans*; klpn = *Klebsiella pneumoniae*; enae = *Enterobacter aerogenes*.

A comparative evaluation was made of the effects of Chemistat II on urinalysis tests. Normal pooled urine samples were added to tubes containing either boric acid, tartaric acid, Chemistat II medium, or nothing (control) and were then inoculated with microorganisms of interest at $1 \times 10^6$ cfu/ml. Urinalysis tests were measured once at Time Zero and, again, after the samples were held for 4, 24, and 48 hours, and 7 days at room temperature. This procedure was also repeated with normal pooled urine samples to which glucose was added at a concentration of about 500 mg/dl, i.e., a concentration routinely found in urine obtained from diabetic patients, so that changes from a positive glucose to a negative glucose over time could be observed. Tables VI and VII summarize comparative results in terms of changes II from Time Zero measurements for Chemistat II, boric acid, and tartaric acid transport systems without and with glucose added, respectively. The comparative tests showed that Chemistat II without added glucose stabilized the urinalysis specimen through 24 hours for all parameters, through 48 hours for all parameters except pH (20° change, e.g., a pH change from 6.0 to 7.0 or from 5.5 to 6.5), and through 7 days for all parameters except pH (2° change) and specific gravity (2° change, e.g., a specific gravity change from 1.005 to 1.015 or 1.015 to 1.025). Chemistat II with glucose held all parameters through 48 hours, and only one organism showed a pH change (2° change) at 7 days. All of the changes observed with Chemistat II were not clinically significant, i.e., would not result in a change in the medical interpretation of the urinalysis results. Comparatively, the boric acid and tartaric acid transport systems without added glucose did not hold specific gravity, pH, nitrites, and blood. Tartaric acid did not hold specific gravity, pH, nitrites, blood, protein, and leukocytes. When glucose was added to the boric acid transport, glucose, pH, nitrites, and blood were not held. The tartaric acid transport system with added glucose did not hold glucose, specific gravity, pH, protein, and nitrites. The degree of change for the boric acid and tartaric acid transport systems with and without glucose added did result in clinically significant changes in the urinalysis results.

TABLE VI

Changes in Urinalysis Results Using Chemistat II, Boric Acid, and Tartaric Acid Transport Systems without Glucose Added

| Degree of Change from Time Zero[b] | Control Transport Time[a] | | | | Boric Acid Transport Time[a] | | | | Tartaric Acid Transport Time[a] | | | | Chemistat II Transport Time[a] | | | |
|---|---|---|---|---|---|---|---|---|---|---|---|---|---|---|---|---|
| | T4 | T24 | T48 | T7d | T4 | T24 | T48 | T7d | T4 | T24 | T48 | T7d | T4 | T24 | T48 | T7d |
| Glucose[c] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Bilirubin[d] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 1 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Ketone[e] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Specific gravity[f] | | | | | | | | | | | | | | | | |
| 2° change | 2 | 12 | 13 | 9 | 0 | 0 | 0 | 2 | 0 | 1 | 5 | 3 | 0 | 0 | 0 | 1 |
| 3° change | 0 | 1 | 2 | 5 | 0 | 0 | 0 | 0 | 0 | 0 | 3 | 8 | 0 | 0 | 0 | 0 |
| ≧4° change | 0 | 0 | 0 | 0 | 0 | 0 | 0 | 0 | 0 | 0 | 1 | 4 | 0 | 0 | 0 | 0 |
| pH[g] | | | | | | | | | | | | | | | | |
| 2° change | 0 | 2 | 3 | 4 | 0 | 0 | 0 | 4 | 0 | 6 | 4 | 3 | 0 | 0 | 1 | 3 |
| 3° change | 0 | 8 | 11 | 8 | 0 | 0 | 0 | 2 | 0 | 1 | 0 | 0 | 0 | 0 | 0 | 0 |
| ≧4° change | 0 | 4 | 15 | 18 | 0 | 0 | 0 | 0 | 0 | 3 | 12 | 18 | 0 | 0 | 0 | 0 |
| Protein[h] | | | | | | | | | | | | | | | | |
| 1° change | 0 | 1 | 5 | 4 | 0 | 0 | 0 | 0 | 0 | 0 | 2 | 3 | 0 | 0 | 0 | 0 |
| 2° change | 0 | 0 | 3 | 8 | 0 | 0 | 0 | 0 | 0 | 0 | 1 | 6 | 0 | 0 | 0 | 0 |
| 3° change | 0 | 0 | 1 | 2 | 0 | 0 | 0 | 0 | 0 | 0 | 0 | 1 | 0 | 0 | 0 | 0 |
| 4° change | 0 | 0 | 1 | 3 | 0 | 0 | 0 | 0 | 0 | 0 | 0 | 0 | 0 | 0 | 0 | 0 |
| Urobilinogin[i] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Nitrites[j] | | | | | | | | | | | | | | | | |
| 1° change | 1 | 53 | 36 | 22 | 1 | 29 | 34 | 8 | 2 | 46 | 39 | 25 | 0 | 0 | 0 | 0 |
| Blood[k] | | | | | | | | | | | | | | | | |
| 1° change | 0 | 2 | 2 | 0 | 0 | 0 | 1 | 2 | 0 | 0 | 0 | 0 | 0 | 0 | 0 | 0 |
| 2° change | 0 | 0 | 0 | 1 | 0 | 0 | 0 | 0 | 0 | 0 | 0 | 1 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |

TABLE VI-continued

Changes in Urinalysis Results Using Chemistat II, Boric Acid, and Tartaric Acid Transport Systems without Glucose Added

| Degree of Change from Time Zero[b] | Control Transport Time[a] | | | | Boric Acid Transport Time[a] | | | | Tartaric Acid Transport Time[a] | | | | Chemistat II Transport Time[a] | | | |
|---|---|---|---|---|---|---|---|---|---|---|---|---|---|---|---|---|
| | T4 | T24 | T48 | T7d | T4 | T24 | T48 | T7d | T4 | T24 | T48 | T7d | T4 | T24 | T48 | T7d |
| Leukocytes[l] | | | | | | | | | | | | | | | | |
| 1° change | 0 | 0 | 0 | 3 | 0 | 0 | 0 | 0 | 0 | 1 | 0 | 4 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |

[a]Transport times: T4 = four hour transport; T24 = twenty-four hour transport; T48 = forty-eight hour transport; T7d = seven day transport; transport time = amount of time elapsed between Time Zero when urine sample was inoculated and when sample was tested for a given parameter.
[b]Degree of change measured from Time Zero: using the scales given for each urinalysis test result listed below, 1° = a change of one step up or down the scale, e.g., for glucose with 250 mg/dl at Time Zero, change to 100 mg/dl or 500 mg/dl; 2° = a change of two steps up or down the scale, e.g., for glucose with 250 mg/dl at Time Zero, change to negative or 1000+ mg/dl; 3° = a change of three steps up or down the scale, e.g., for glucose with 100 mg/dl at Time Zero, change to 1000+ mg/dl; and 4° = a change of four steps up or down the scale, e.g., for glucose with 1000+ mg/dl at Time Zero, change to negative.
[c]Possible urinalysis test results for glucose: negative, 100, 250, 500, or 1000+ mg/dl.
[d]Possible urinalysis test results for bilirubin: negative, small, moderate, or large.
[e]Possible urinalysis test results for ketone: negative, trace, small, moderate, or large.
[f]Possible urinalysis test results for specific gravity: ≧1.005, 1.010, 1.015, 1.020, 1.025, or ≧1.030.
[g]Possible urinalysis test results for pH: ≧5.5, 6.0, 6.5, 7.0, 7.5, 8.0, 8.5, or ≧9.0.
[h]Possible urinalysis test results for protein: negative, trace, 30, 100, 300, or 1000+ mg/dl.
[i]Possible urinalysis test results for urobilinogen: 0.2, 1, 2, 4, or 8 mg/dl.
[j]Possible urinalysis test results for nitrites: negative or positive.
[k]Possible urinalysis test results for blood: negative, trace, small, moderate or large.
[l]Possible urinalysis test results for leukocytes: negative, trace, small, moderate or large.

TABLE VII

Changes in Urinalysis Results Using Chemistat II, Boric Acid, and Tartaric Acid Transport Systems with Glucose Added

| Degree of Change from Time Zero[b] | Control Transport Time[a] | | | | Boric Acid Transport Time[a] | | | | Tartaric Acid Transport Time[a] | | | | Chemistat II Transport Time[a] | | | |
|---|---|---|---|---|---|---|---|---|---|---|---|---|---|---|---|---|
| | T4 | T24 | T48 | T7d | T4 | T24 | T48 | T7d | T4 | T24 | T48 | T7d | T4 | T24 | T48 | T7d |
| Glucose[c] | | | | | | | | | | | | | | | | |
| 1° change | 0 | 4 | 8 | 10 | 0 | 0 | 0 | 3 | 0 | 0 | 1 | 3 | 0 | 0 | 0 | 0 |
| 2° change | 0 | 0 | 7 | 12 | 0 | 0 | 1 | 1 | 0 | 0 | 0 | 0 | 0 | 0 | 0 | 0 |
| 3° change | 0 | 0 | 2 | 8 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Bilirubin[d] | | | | | | | | | | | | | | | | |
| 1° change | 0 | 0 | 0 | 1 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Ketone[e] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Specific gravity[f] | | | | | | | | | | | | | | | | |
| 2° change | 1 | 2 | 6 | 15 | 0 | 0 | 0 | 0 | 0 | 0 | 0 | 3 | 0 | 0 | 0 | 0 |
| 3° change | 0 | 0 | 0 | 1 | 0 | 0 | 0 | 0 | 0 | 0 | 0 | 5 | 0 | 0 | 0 | 0 |
| ≧4° change | 0 | 0 | 0 | 0 | 0 | 0 | 0 | 0 | 0 | 0 | 0 | 0 | 0 | 0 | 0 | 0 |
| pH[g] | | | | | | | | | | | | | | | | |
| 2° change | 2 | 15 | 12 | 7 | 0 | 0 | 0 | 3 | 0 | 0 | 3 | 13 | 0 | 0 | 0 | 1 |
| 3° change | 0 | 0 | 14 | 7 | 0 | 0 | 0 | 1 | 0 | 0 | 0 | 2 | 0 | 0 | 0 | 0 |
| ≧4° change | 0 | 0 | 8 | 27 | 0 | 0 | 0 | 0 | 0 | 0 | 2 | 4 | 0 | 0 | 0 | 0 |
| Protein[h] | | | | | | | | | | | | | | | | |
| 1° change | 0 | 0 | 0 | 1 | 0 | 0 | 0 | 0 | 0 | 0 | 1 | 1 | 0 | 0 | 0 | 0 |
| 2° change | 0 | 0 | 0 | 2 | 0 | 0 | 0 | 0 | 0 | 0 | 0 | 2 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 4 | 0 | 0 | 0 | 0 |

TABLE VII-continued

Changes in Urinalysis Results Using Chemistat II, Boric Acid,
and Tartaric Acid Transport Systems with Glucose Added

| Degree of Change from Time Zero[b] | Control Transport Time[a] | | | | Boric Acid Transport Time[a] | | | | Tartaric Acid Transport Time[a] | | | | Chemistat II Transport Time[a] | | | |
|---|---|---|---|---|---|---|---|---|---|---|---|---|---|---|---|---|
| | T4 | T24 | T48 | T7d | T4 | T24 | T48 | T7d | T4 | T24 | T48 | T7d | T4 | T24 | T48 | T7d |
| Urobilinogin[i] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Nitrites[j] | | | | | | | | | | | | | | | | |
| 1° change | 0 | 2 | 1 | 1 | 0 | 4 | 10 | 3 | 0 | 13 | 6 | 1 | 0 | 0 | 0 | 0 |
| Blood[k] | | | | | | | | | | | | | | | | |
| 1° change | 0 | 0 | 0 | 0 | 0 | 0 | 0 | 2 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |
| Leukocytes[l] | | | | | | | | | | | | | | | | |
| 1° change | 0 | 0 | 0 | 0 | 0 | 0 | 0 | 0 | 0 | 0 | 0 | 0 | 0 | 0 | 0 | 0 |
| 2° change | 0 | 0 | 0 | 0 | 0 | 0 | 0 | 0 | 0 | 0 | 0 | 0 | 0 | 0 | 0 | 0 |
| 3° change | 0 | 0 | 0 | 0 | 0 | 0 | 0 | 0 | 0 | 0 | 0 | 0 | 0 | 0 | 0 | 0 |
| 4° change | 0 | 0 | 0 | 0 | 0 | 0 | 0 | 0 | 0 | 0 | 0 | 0 | 0 | 0 | 0 | 0 |

[a]Transport times: T4 = four hour transport; T24 = twenty-four hour transport; T48 = forty-eight hour transport; T7d = seven day transport; transport time = amount of time elapsed between Time Zero when urine samples were inoculated and when urine samples were tested for a given parameter.
[b]Degree of change measured from Time Zero: using the scales given for each urinalysis test result listed below, 1° = a change of one step up or down the scale, e.g., for glucose with 250 mg/dl at Time Zero, change to 100 mg/dl or 500 mg/dl; 2° = a change of two steps up or down the scale, e.g., for glucose with 250 mg/dl at Time Zero, change to negative or 1000+ mg/dl; 3° = a change of three steps up or down the scale, e.g., for glucose with 100 mg/dl at Time Zero, change to 1000+ mg/dl; and 4° = a change of four steps up or down the scale, e.g., for glucose with 1000+ mg/dl at Time Zero, change to negative.
[c]Possible urinalysis test results for glucose: negative, 100, 250, 500, or 1000+ mg/dl.
[d]Possible urinalysis test results for bilirubin: negative, small, moderate, or large.
[e]Possible urinalysis test results for ketone: negative, trace, small, moderate, or large.
[f]Possible urinalysis test results for specific gravity: ≧1.005, 1.010, 1.015, 1.020, 1.025, or ≧1.030.
[g]Possible urinalysis test results for pH: ≧5.5, 6.0, 6.5, 7.0, 7.5, 8.0, 8.5, or ≧9.0.
[h]Possible urinalysis test results for protein: negative, trace, 30, 100, 300, or 1000+ mg/dl.
[i]Possible urinalysis test results for urobilinogen: 0.2, 1, 2, 4, or 8 mg/dl.
[j]Possible urinalysis test results for nitrites: negative or positive.
[k]Possible urinalysis test results for blood: negative, trace, small, moderate or large.
[l]Possible urinalysis test results for leukocytes: negative, trace, small, moderate or large.

Another group of liquid stabilizing transport/preservative formulations which are inert to plastics, rubber, and silicone, hereinafter referred to as "Chemistat III", have been found, comprising an antimicrobial organic acid, boric acid, and a biguanide. Preferably, Chemistat III comprises an antimicrobial propionate, boric acid, and a biguanide. Most preferably, Chemistat III formulations comprise from about 2.5 mg/ml to about 7.5 mg/ml sodium proprionate, from about 0.1 mg/ml to about 10 mg/ml boric acid, and from about 0.01 mg/ml to about 0.1 mg/ml chlorhexidine, and any combination thereof. For preservation of urine samples, a preferred Chemistat III formulation comprises 6.25 mg/ml sodium proprionate, 0.5 mg/ml boric acid, and 0.025 mg/ml chlorhexidine.

EXAMPLE 3

Effectiveness of Chemistat III Formulations

Chemistat III formulations were shown to preserve urine samples containing significant microbial contamination and at the same time maintain the chemical and physical properties of the urine samples.

Table VIII gives the antimicrobial data for the individual components of Chemistat III. As previously discussed, chlorhexidine alone had cidal activity against *Escherichia coli* and *Candida albicans* at 0.0075 mg/ml; *Enterobacter aerogenes*, at 0.01 mg/ml; *Proteus vulgaris* and *Klebsiella pneumoniae*, at 0.02 mg/ml; showed variable cidal activity against *Enterococcus faecalis* at 0.05–0.8 mg/ml; and was not cidal against *Pseudomonas aeruginosa* at up to 0.05 mg/ml. Sodium propionate was inhibitory against *Pseudomonas aeruginosa* and *Enterococcus faecalis* at 10 mg/ml, but was ineffective against *Escherichia coli, Proteus vulgaris, Candida albicans, Klebsiella pneumoniae*, and *Enterobacter aerogenes* at up to 10 mg/ml. Boric acid was ineffective against *Escherichia coli, Pseudomonas aeruginosa, Enterococcus faecalis*, and *Enterobacter aerogenes*. Thus, the components of the Chemistat III formulations when used alone were unable to control the growth of the microorganisms of interest.

TABLE VIII

Antimicrobial Activity for Individual Chemistat III Components

| Component | Survival Values[a] after 24 hours at Room Temperature for Representative Organisms[b] | | | | | | |
|---|---|---|---|---|---|---|---|
| | esco | psae | prvu | enfa | caal | klpn | enae |
| Chlorhexidine (0.005 mg/ml) | 0.003 | tntc | | 1.115 | 5.308 | | tntc |
| Chlorhexidine (0.0075 mg/ml) | 0.000 | 4.049 | | 0.598 | 0.000 | | 6.098 |
| Chlorhexidine (0.01 mg/ml) | 0.000 | 0.277 | | 0.520 | | | 0.000 |
| Chlorhexidine (0.02 mg/ml) | 0.000 | 0.275 | 0.000 | 0.179 | | | |
| Chlorhexidine (0.02 mg/ml) | 0.000 | 0.080 | 0.000 | 0.141 | 0.000 | 0.000 | |
| Chlorhexidine (0.05 mg/ml) | 0.000 | 0.046 | | 0.000 | 0.000 | | 0.000 |
| Chlorhexidine (0.1 mg/ml) | 0.000 | | | 0.561 | 0.000 | | |
| Chlorhexidine (0.8 mg/ml)[c] | 0.000 | | | 0.000 | 0.000 | | |
| Boric Acid (5 mg/ml) | 0.770 | 1.157 | | 2.647 | | | 1.061 |
| Sodium propionate (5 mg/ml) | tntc | tntc | tntc | tntc | tntc | tntc | |
| Sodium propionate (10 mg/ml) | tntc | 0.341 | | 2.702 | | | |

[a]Numbers indicate survival values (number of organisms recovered after 24 hours incubation at room temperature divided by the initial control count; tntc = organisms at 24 hours too numerous to count.
[b]Organism Key: esco = *Escherichia coli*; psae = *Pseudomonas aeruginosa*; prvu = *Proteus vulgaris*; enfa = *Enterococcus faecalis*; caal = *Candida albicans*; klpn = *Klebsiella pneumoniae*; enae = *Enterobacter aerogenes*.
[c]Produced a false positive protein upon urinalysis.

TABLE IX

Antimicrobial Activity for Chemistat III Component Combinations

| Component Combinations | Survival Values[a] after 24 hours at Room Temperature for Representative Organisms[b] | | | | | | |
|---|---|---|---|---|---|---|---|
| | esco | psae | prvu | enfa | caal | klpn | enae |
| Chlorhexidine (0.02 mg/ml); sodium propionate (10 mg/ml) | 0.000 | 0.005 | 0.000 | 0.448 | | | |
| Sodium propionate (5 mg/ml); chlorhexidine (0.02 mg/ml) | 0.000 | 0.326 | 0.000 | 0.605 | 0.000 | 0.000 | |
| Boric Acid (1 mg/ml); chlorhexidine (0.005 mg/ml) | 0.000 | 2.304 | | 1.231 | 0.000 | | 1.861 |
| Chlorhexidine (0.02 mg/ml); sodium propionate (10 mg/ml); boric acid (5 mg/ml) | 0.000 | 0.000 | 0.000 | | 0.020 | | |

[a]Numbers indicate survival values (number of organisms recovered after 24 hours incubation at room temperature divided by the initial control count; tntc = organisms at 24 hours too numerous to count.
[b]Organism Key: esco = *Escherichia coli*; psae = *Pseudomonas aeruginosa*; prvu = *Proteus vulgaris*; enfa = *Enterococcus faecalis*; caal = *Candida albicans*; klpn = *Klebsiella pneumoniae*; enae = *Enterobacter aerogenes*.

Table IX presents antimicrobial data for Chemistat III component combinations. Boric acid (1 mg/ml) and chlorhexidine (0.005 mg/ml) in combination was not cidal against *Pseudomonas aeruginosa, Enterococcus faecalis*, and *Enterobacter aerogenes*. Likewise, sodium propionate (5 mg/ml) and chlorhexidine (0.02 mg/ml) in combination was not cidal against *Pseudomonas aeruginosa* and *Enterococcus faecalis*. When chlorhexidine (0.02 mg/ml), sodium propionate (10 mg/ml) and boric acid (5 mg/ml) were combined, the composition was cidal against the microorganisms of interest given in Table IX and did not interfere with urinalysis (data not shown).

It is to be understood that the examples presented herein are merely representative of the transport/preservative formulations of the present invention characterized as being cidal against the microorganisms of interest and not altering the chemical and physical properties of the sample, and that the scope of the invention extends to other combinations of antimicrobial aromatic alcohols, alkyl guaiacols, biguanides, organic acids, lipid membrane-disrupting agents, and boric acid derivatives. While the examples demonstrated the stabilization of urine samples contaminated with microorganisms commonly found in urine, it is to be further understood that the transport/preservative system of the present invention can be applied to the preservation of other patient samples, bodily fluids, biological reagents, therapeutics, and personal care products, and that preferred combinations and concentrations of components in the formulations of the present invention for these applications can be easily determined by following the teachings presented in the examples.

The transport/preservative system of the present invention maintains the chemical and physical integrity of patient specimens or bodily fluids during extended transport. Examples of the patient specimens for which the transport system is effective include but are not limited to urine, saliva, sputum, and tissue biopsies.

Samples submitted for DNA or RNA analysis or PCR probe technology can also be preserved without the transport/preservative system of the present invention. While major efforts have been made in DNA/RNA analysis and PCR probe technology to block inhibitors of the critical reactions and to block the negative action of DNase and RNase. However, no efforts have been made to block the potential negative effects of growth and/or metabolism of organisms in the sample. Growth or metabolism can drastically affect both probe technology and PCR, because it can alter the chemical properties of the sample. Also, live organisms can excrete DNase and RNase. These samples must be processed immediately after sampling, or they must have a suitable preservative added which will kill the microorganisms. The cidal action of the transport/preservative system of the present invention provides the necessary killing action.

The transport/preservative system of the present invention can also be used for stabilizing biological reagents. For example, numerous assay methodologies routinely used for both diagnostic and research purposes require reagents that contain substances capable of supporting the growth of contaminating microorganisms. Thus, the reagents are susceptible to both physical and chemical degradation caused by the growth and/or metabolism of contaminating microorganisms. Examples of such reagents include but are not limited to starting materials, catalysts, cofactors, surface-active agents, nuclei acid, protein, carbohydrate, and lipid standards, antigen-antibody reagents, genetic markers and probes including those used in PCR technology, and detection compositions. The chemical composition of such reagents include but are not limited to amino acids, carbohydrates, fatty acids, nucleic acids, proteins, polysaccharides, lipids, sugars, and mixtures and/or complex thereof.

The present invention also includes a device which comprises an accessible, sealable enclosure for containing and preserving a sample which may contain microorganisms which enclosure contains a composition free of toxins including mercury, mercury containing compounds, formaldehyde, formaldehyde releasing compounds, and azides which are unsuitable for use in high volume processing and comprises a biguanide and one or more additional antimicrobial agents, wherein the composition is cidal to microorganisms when present in the sample. This device is for the preservation of a sample selected from a patient sample, a bodily fluid such as urine, tissue specimen, and reagent, a biological reagent, a therapeutic, or a personal care product. The preferred biguanide in the device is chlorhexidine. One preferred composition useful in the device comprises an aromatic alcohol such as 2-phenyl ethanol, a terpenoid such as isoeugenol, and a biguanide such as chlorhexidine. Another preferred composition comprises an organic acid such as sodium propionate, a parahydroxybenzoate such as ethyl parahydroxybenzoate, and a biguanide such as chlorhexidine. Yet another preferred composition comprises a propionate such as sodium propionate, boric acid and/or boric acid derivative, and a biguanide such as chlorhexidine.

The transport/preservative system of the present invention is effective in the preservation of aqueous or alcoholic therapeutics including pharmaceuticals, nutraceuticals and over-the-counter preparations which contain substances capable of supporting the growth of contaminating microorganisms. Examples of therapeutics preserved by the present invention include but are not limited to vaccines, antigen preparations for allergy treatment, hormone preparations, insulin, nasal sprays, liquid cough and cold remedies, liquid allergy medications, and liquid vitamin and nutrient preparations.

Personal care products can also be preserved from chemical and/or physical degradation using the transport/preservation system of the present invention. Examples of personal care products preserved by the present invention include but are not limited to cosmetics, hand cleansers, lotions, shampoos and contact lens solutions.

The transport/preservation formulations can also be used as sanitizers for surfaces, equipment, and appliances. Upon application of a sanitizer comprising the transport/preservative formulation, a residue remains which reduces the microbial bioburden over time.

I claim:

1. In a method for preserving a sample of urine which may contain microorganisms comprising:

preserving the chemical and physical properties of said sample by mixing said sample with an effective amount of a composition comprising a biguanide and at least one other antimicrobial agent, wherein said composition is cidal to said microorganisms when present in said sample.

2. The method of claim 1, wherein said biguanide is chlorhexidine.

3. The method of claim 1, wherein said at least one other antimicrobial agent comprises an agent that reduces the selective permeability of the cell membrane of said microorganisms.

4. The method of claim 2, wherein said at least one other antimicrobial agent comprises an agent that reduces the selective permeability of the cell membrane of said microorganisms.

5. The method of claim 1, wherein said at least one other antimicrobial agent comprises a propionate.

6. The method of claim 2, wherein said at least one other antimicrobial agent comprises a propionate.

7. The method of claim 5, wherein said propionate is sodium propionate.

8. The method of claim 6, wherein said propionate is sodium propionate.

9. The method of claim 5, wherein said composition further comprises a parahydroxybenzoate.

10. The method of claim 6, wherein said composition further comprises a parahydroxybenzoate.

11. The method of claim 7, wherein said composition further comprises a parahydroxybenzoate.

12. The method of claim 8, wherein said composition further comprises a parahydroxybenzoate.

13. The method of claim 9, wherein said parahydroxybenzoate is ethyl parahydroxybenzoate.

14. The method of claim 10, wherein said parahydroxybenzoate is ethyl parahydroxybenzoate.

15. The method of claim 11, wherein said parahydroxybenzoate is ethyl parahydroxybenzoate.

16. The method of claim 12, wherein said parahydroxybenzoate is ethyl parahydroxybenzoate.

17. A method for preserving a urine sample which may contain microorganisms comprising:

mixing said urine sample with a composition, said composition including said sample having a concentration of (a) about 0.01 to 0.1 mg/ml of chlorhexidine and (b) about 0.1 to 0.7 mg/ml ethyl paraben.

18. A method for preserving a urine sample which may contain microorganisms comprising:

mixing said urine sample with a composition, said composition including said sample having a concentration of (a) about 0.01 to 0.1 mg/ml chlorhexidine and (b) about 1 to 10 mg/ml sodium propionate.

19. The method of claim 18, wherein said composition including said sample has a concentration of about 0.1 to 1.0 mg/ml ethyl paraben.

20. The method of claim 18, wherein said composition including said sample has a concentration of about 0.25 to 1 mg/ml boric acid.

21. A method for preserving a urine sample which may contain microorganisms comprising:

mixing said urine sample with a composition, said composition including said sample having a concentration of (a) about 0.01 to 0.1 mg/ml of chlorhexidine, (b) about 0 to 2.5 µl/ml 2 phenyl ethanol, and (c) about 0.2 to 1.5 µl/ml isoeugenol.

22. A method for preserving a urine sample which may contain microorganisms comprising:

mixing said urine sample with a composition consisting essentially of chlorhexidine and ethyl paraben, said composition including said sample having a concentration of (a) about 0.01 to 0.1 mg/ml of chlorhexidine and (b) about 0. 1 to 1 mg/ml ethyl paraben.

23. A method for preserving a urine sample which may contain microorganisms comprising:

mixing said urine sample with a composition consisting essentially of chlorhexidine and sodium propionate, said composition including said sample having a concentration of (a) about 0.01 to 0.1 mg/ml chlorhexidine and (b) about 1 to 10 mg/ml sodium propionate.

24. A method for preserving a urine sample which may contain microorganisms comprising:

mixing said urine sample with a composition consisting essentially of chlorhexidine, sodium propionate and ethyl paraben, said composition including said sample having a concentration of (a) about 0.01 to 0.1 mg/ml chlorhexidine, (b) about 1 to 10 mg/ml sodium propionate and (c) about 0.1 to 1 mg/ml ethyl paraben.

25. A method for preserving a urine sample which may contain microorganisms comprising:

mixing said urine sample with a composition consisting essentially of chlorhexidine, sodium propionate and boric acid, said composition including said sample having a concentration of (a) about 0.01 to 0.1 mg/ml chlorhexidine, (b) about 1 to 10 mg/ml sodium propionate and (c) about 0.25 to 1 mg/ml boric acid.

26. A method for preserving a urine sample which may contain microorganisms comprising:

mixing said urine sample with a composition consisting essentially of chlorhexidine, 2 phenyl ethanol, and isoeugenol, said composition including said sample having a concentration of (a) about 0.01 to 0.1 mg/ml of chlorhexidine, (b) about 0 to 2.5 µl/ml 2 phenyl ethanol) and (c) about 0.2 to 1.5 µl/ml isoeugenol.

27. A method for preserving a urine sample which may contain microorganisms comprising:

mixing said urine sample with a composition consisting essentially of chlorhexidine, sodium propionate, and boric acid, said composition including said sample having a concentration of (a) about 0.01 to 0. 1 mg/ml of chlorhexidine, (b) about 2.5 to 7.5 mg/ml sodium propionate, and (c) about 0.1 mg/ml to about 10 mg/ml boric acid.

28. The method of claim 19, wherein said composition including said sample has a concentration of about 2.5 mg/ml to about 7.5 mg/ml sodium propionate, about 0.1 mg/ml to about 1 mg/ml ethyl parahydroxybenzoate, and about 0.01 mg/ml to about 0.1 mg/ml chlorhexidine.

* * * * *